(12) United States Patent
Aoki et al.

(10) Patent No.: US 9,846,813 B2
(45) Date of Patent: Dec. 19, 2017

(54) IMAGE PICKUP DEVICE

(71) Applicants: FUJITSU LIMITED, Kawasaki-shi, Kanagawa (JP); FUJITSU FRONTECH LIMITED, Inagi-shi, Tokyo (JP)

(72) Inventors: Takahiro Aoki, Kawasaki (JP); Soichi Hama, Atsugi (JP); Isao Iwaguchi, Inagi (JP)

(73) Assignees: FUJITSU LIMITED, Kawasaki (JP); FUJITSU FRONTECH LIMITED, Tokyo (JP)

( * ) Notice: Subject to any disclaimer, the term of this patent is extended or adjusted under 35 U.S.C. 154(b) by 0 days.

(21) Appl. No.: 15/051,200

(22) Filed: Feb. 23, 2016

(65) Prior Publication Data
US 2016/0275362 A1 Sep. 22, 2016

(30) Foreign Application Priority Data
Mar. 20, 2015 (JP) .................. 2015-058721

(51) Int. Cl.
*G06K 9/62* (2006.01)
*G06K 9/00* (2006.01)
(Continued)

(52) U.S. Cl.
CPC ........ *G06K 9/00885* (2013.01); *A61B 5/0077* (2013.01); *A61B 5/117* (2013.01);
(Continued)

(58) Field of Classification Search
CPC ............ G06K 2009/0006; G06K 2009/00932; G01N 2021/217; G01N 2021/495; G06T 2207/30101–2207/30104
See application file for complete search history.

(56) References Cited

U.S. PATENT DOCUMENTS 5,847,394 A * 12/1998 Alfano ............... A61B 1/042
250/341.1
6,404,904 B1 6/2002 Einighammer et al.
(Continued)

FOREIGN PATENT DOCUMENTS

DE 198 18 229 A1 10/1999
JP 2002-200050 7/2002
(Continued)

OTHER PUBLICATIONS

Stephen P. Morgan et al., "Rotating orthogonal polarization imaging", Jul. 1, 2008 / vol. 33, No. 13 / Optics Letters, Optical Society, pp. 1503-1505.*
(Continued)

*Primary Examiner* — Brian P Werner
(74) *Attorney, Agent, or Firm* — Staas & Halsey LLP

(57) ABSTRACT

A device includes an illumination device that casts light of a prescribed polarization direction on a scattering body, a camera that picks up images of the scattering body at a plurality of different polarization angles, and a processor that executes a process of generating and outputting an inner layer image, of an inner layer of an inside of the scattering body, in response to a depth from a surface of the scattering body on the basis of the images of the scattering body picked up at the plurality of different polarization angles.

6 Claims, 9 Drawing Sheets

(51) Int. Cl.
  *A61B 5/117* (2016.01)
  *G01N 21/47* (2006.01)
  *G06K 9/20* (2006.01)
  *A61B 5/00* (2006.01)

(52) U.S. Cl.
  CPC ......... *A61B 5/489* (2013.01); *G01N 21/4795* (2013.01); *G06K 9/209* (2013.01); *G06K 9/2036* (2013.01); *G06K 9/6201* (2013.01); *G06K 2009/00932* (2013.01)

(56) References Cited

U.S. PATENT DOCUMENTS

| | | | | |
|---|---|---|---|---|
| 2011/0211047 | A1* | 9/2011 | Chhibber | A61B 5/0059 348/47 |
| 2012/0230551 | A1 | 9/2012 | Hama et al. | |
| 2014/0028825 | A1* | 1/2014 | Yamagata | H04N 5/2621 348/77 |
| 2015/0356339 | A1* | 12/2015 | Demos | H04N 7/18 348/77 |

FOREIGN PATENT DOCUMENTS

| | | |
|---|---|---|
| JP | 2010-218258 | 9/2010 |
| JP | 2012-187150 | 10/2012 |
| KR | 10-2013-0123426 | 11/2013 |
| KR | 10-2014-0079180 | 6/2014 |
| WO | 2012/104784 | 8/2012 |

OTHER PUBLICATIONS

Rehn et al., "Depth probing of diffuse tissues controlled with elliptically polarized light", Journal of Biomedical Optics, vol. 18, SPIE, SPEIDigitalLibrary.org/jbo, Jan. 2013, 6 pages.

Extended European Search Report dated Jul. 28, 2016 in corresponding European Patent Application No. 16156914.0.

Photonic Lattice, Inc. PI-110, [online] [Searched on Feb. 19, 2015], the Internet <URl:http://www.photonic-lattice.com/ja/products/polarization_camera/pi-110/>.

Bicout, Dominique J. and George H. Weiss, "A measure of photon penetration into tissue in diffusion models", *Optics Communications*, vol. 158, Issues 1-6, Dec. 15, 1998, pp. 213-220.

Korean Office Action dated Mar. 24, 2017, in corresponding Korean Patent Application No. 10-2016-0028389.

* cited by examiner

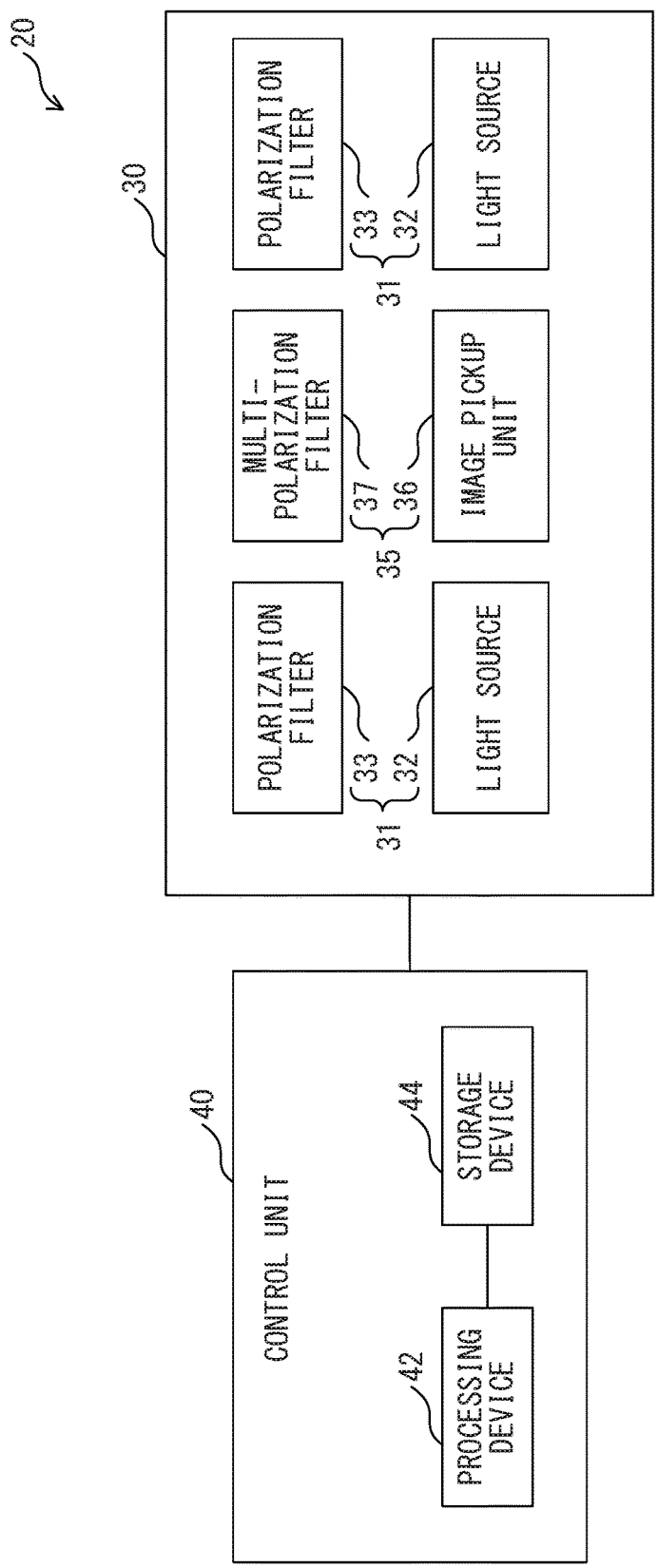
F I G. 1

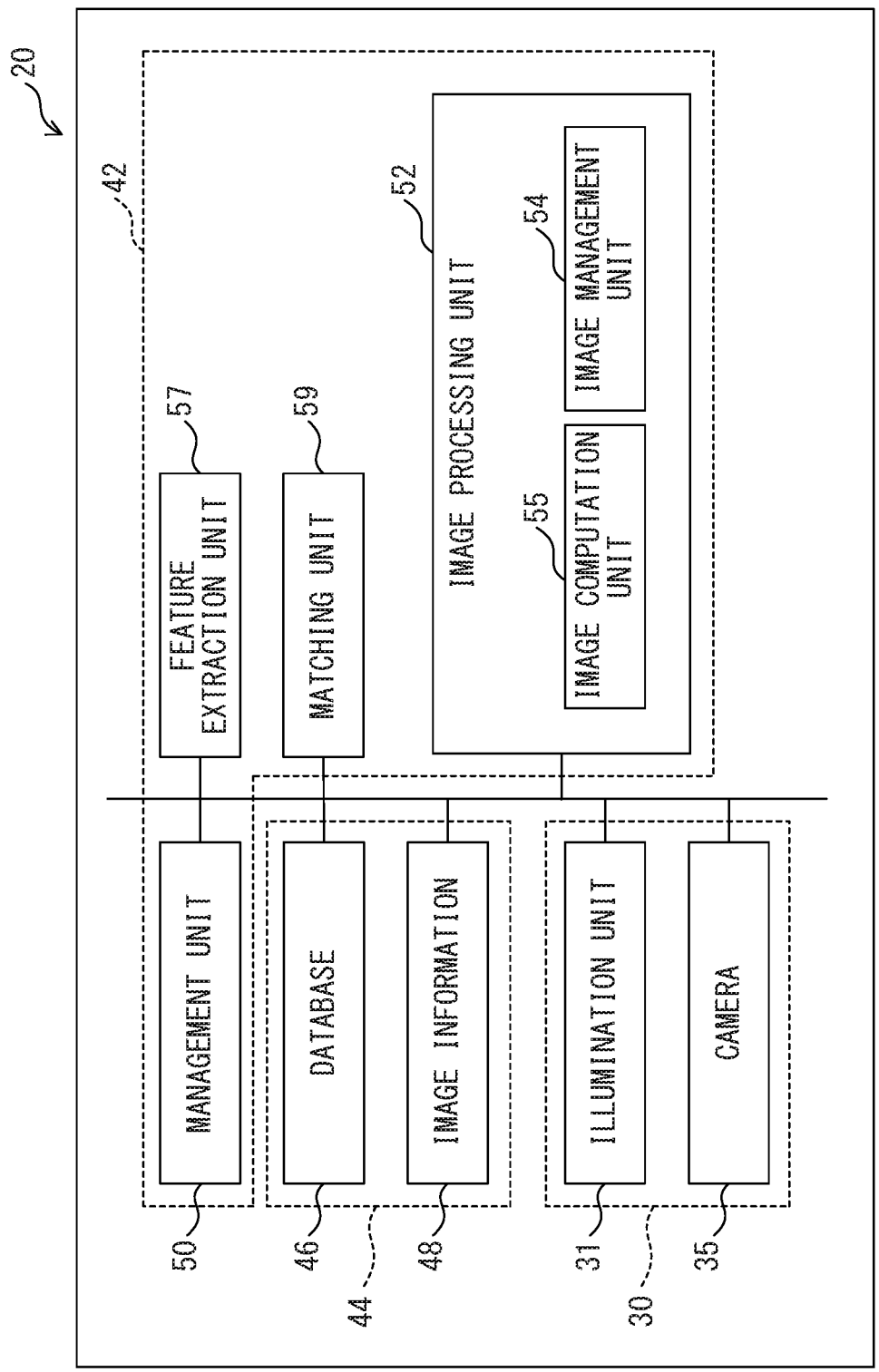
F I G. 2

| CATEGORY | CALCULATION METHOD | USE METHOD | |
|---|---|---|---|
| SURFACE REFLECTION | $I_C(0°)-(I_C(45°)+I_C(135°)-I_C(90°))$ | SURFACE INFORMATION (PALM PRINT INFORMATION) | |
| INFORMATION OF SHALLOW POSITION | $I_C(45°)+I_C(135°)-I_C(90°)$ | INNER LAYER INFORMATION | SHALLOW INFORMATION |
| INFORMATION OF DEEP POSITION | $I_C(90°)$ | | DEEP INFORMATION (VEIN INFORMATION) |

FIG. 7

IMAGE PICKUP DEVICE

CROSS-REFERENCE TO RELATED APPLICATION

This application is based upon and claims the benefit of priority of the prior Japanese Patent Application No. 2015-058721, filed on Mar. 20, 2015, the entire contents of which are incorporated herein by reference.

FIELD

The embodiments discussed herein are related to an image pickup device.

BACKGROUND

As a technique that uses an image pickup device, for example a biometric authentication device that authenticates individuals by using palm vein etc. is known. An example is known in which linearly polarized light in a particular polarization direction is cast on a biological body and in that state, an optical reduction system including a lens array is used so as to remove components of an ommatidium image obtained by a lens provided with an analyzer that transmits only polarized light components in a particular polarization direction from an ommatidium image obtained by a lens not provided with such an analyzer. Also, an example including an image pickup unit for picking up an image of a biological body by using the light reflected from the biological body and an extraction unit for extracting a frequency component higher than a prescribed spatial frequency from an biological body image picked up by the image pickup unit is also known (for example Patent Documents 1 and 2).

As another example of a technique using an image pickup device, an example below for measuring highly accurately pigment compositions such as melanin components, hemoglobin components, etc. contributing to the skin colors is also known. Specifically, it is an example in which the surface-reflected light components, which are noise components, are removed by using polarization, so that pigment compositions such as melanin components, hemoglobin components, etc. are obtained for internal light components (for example Patent Document 3).

Further, an example of a camera that observes polarized light is known (for example non Patent Document 1). An example is also known in which a probability density function that represents the depth in a biological body from which light returns is calculated by diffusion approximation (for example, non Patent Document 2).
[Patent Document 1] Japanese Laid-open Patent Publication No. 2010-218258
[Patent Document 2] Japanese Laid-open Patent Publication No. 2012-187150
[Patent Document 3] Japanese Laid-open Patent Publication No. 2002-200050
[non Patent Document 1] Photonic Lattice, Inc. PI-110, [online] [Searched on Feb. 19, 2015], the Internet <URL: http://www.photonic-lattice.com/ja/products/polarization_camera/pi-110/>
[non Patent Document 2] A measure of photon penetration into tissue in diffusion models, Optics Communications, Volume 158, Issues 1-6, 15 Dec. 1998, Pages 213-220, by Dominique J. Bicout, George H. Weiss

SUMMARY

An image pickup device according to an aspect includes an illumination device that casts light of a prescribed polarization direction on a scattering body, a camera that picks up images of the scattering body at a plurality of different polarization angles, and a processor that executes a process of generating and outputting an inner layer image, of an inner layer of an inside of the scattering body, in response to a depth from a surface of the scattering body on the basis of the images of the scattering body picked up at the plurality of different polarization angles.

The object and advantages of the invention will be realized and attained by means of the elements and combinations particularly pointed out in the claims.

It is to be understood that both the foregoing general description and the following detailed description are exemplary and explanatory and are not restrictive of the invention.

BRIEF DESCRIPTION OF DRAWINGS

FIG. 1 illustrates an example of a configuration of an image pickup device according to the first embodiment;
FIG. 2 illustrates an example of a functional configuration of the image pickup device according to the first embodiment;
FIG. 7 illustrates an example of a type of an image obtained by the image pickup method according to the first embodiment.

DESCRIPTION OF EMBODIMENTS

Figure 3:
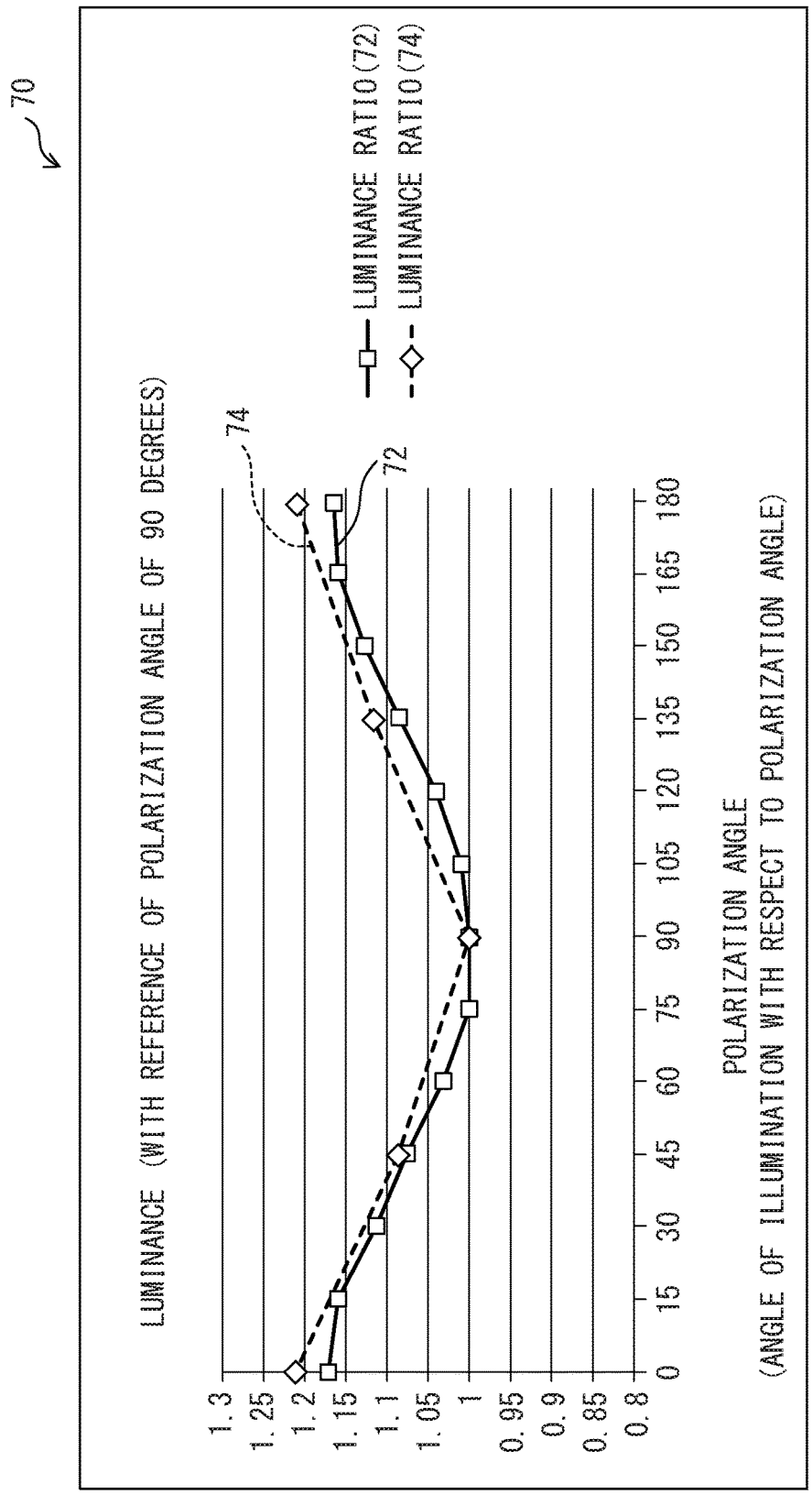
FIG. 3 illustrates an example of the polarization angle dependence of incident light of the luminance value of a subject.

A palm vein authentication device picks up an image of the vein pattern in a biological body by using near infrared rays so as to authenticate an individual. However, biological bodies have characteristics that cause a high level of scattering with respect to near infrared rays, sometimes resulting in a case when the above conventional method fails to obtain highly accurate information due to the scattering. In a method in which for example light polarized in a certain direction is cast and the light in the same polarization state as the cast light is removed for obtaining information of the inside of a biological body, the light in the same polarization state as the illumination light is also removed due to the scattering light from the inside, sometimes preventing highly accurate images from being obtained. Accordingly, it is desired that information of an inner layer in response to the depth from the surface of the scattering body be obtained highly accurately.

First Embodiment

Hereinafter, explanations will be given for an image pickup device 20 according to a first embodiment by referring to the drawings. In the present embodiment, the image pickup device 20 is explained as a device that conducts biometric authentication by using a picked up image. FIG. 1 illustrates an example of a configuration of the image pickup device 20 according to the first embodiment. As illustrated in FIG. 1, the image pickup device 20 includes an optical unit 30 and a control unit 40. The optical unit 30 casts, on a scattering body serving as a subject, light in a prescribed polarization direction (also referred to as prescribed polarized light hereinafter) so as to pick up images in a plurality of polarization directions. The control unit 40 controls the operations of the image pickup device 20. The optical unit 30 and the control unit 40 may be integrated. An example of the image pickup device 20 may be a multifunctional mobile phone, a tablet information processing apparatus, etc.

The optical unit 30 includes illumination units 31 and a camera 35. The illumination unit 31 includes a light source 32 and a polarization filter 33, and outputs prescribed polarized light for picking an image of the scattering body. The light source 32 may be for example a Light Emitting Diode (LED). Devices other than an LED can also be used as the light source 32. The polarization filter 33 is a polarization filter for illumination, and is a polarization filter that transmits polarized light in a particular direction. It is assumed that the angle representing the polarization direction of the polarization filter 33 is expressed by polarization angle θ=0. Note that the purpose of FIG. 1 including two light sources 32 is to illustrate an example in which the light sources 32 and the polarization filters 33 are arranged to form a circle around the camera 35, and thereby light is cast evenly on the scattering body serving as the subject.

The camera 35 includes an image pickup unit 36 and a multi-polarization filter 37. The image pickup unit 36 includes a lens and an image pickup element, convers the light incident via the lens into an electric signal, and thereby picks up an image. The multi-polarization filter 37 is a filter that has the function of transmitting light in a plurality of polarization directions. The multi-polarization filter 37 may be a filter having a polarization function corresponding to polarization angles θ=0° (0 degree), 45° (45 degrees), 90° (90 degrees) and 135° (135 degrees) for each pixel, like for example a filter included in the camera described in non Patent Document 1. Note that polarization angle θ is not limited to the above example. Also, the multi-polarization filter 37 may employ a different configuration such as one in which one filter with a variable polarization angle or a plurality of filters with different polarization angles are attached or detached.

In the present embodiment, explanations will be given for an example in which polarization angels θ=0°, 45°, 90° and 135° are used as the polarization angle θ of the light picked up by the camera 35. The camera 35 picks up the light reflected from the scattering body serving as the subject. For the picking up, images in different polarization directions are output independently. Specifically, images at polarization angles θ=0°, 45°, 90° and 135° are output in the present embodiment.

The control unit 40 includes a processing device 42 and a storage device 44. The processing device 42 (a processor for example) includes a computation processing unit for performing various types of processes for controlling the operation of the image pickup device 20. The storage device 44 is a storage device that stores a program and that the processing device 42 uses as a work area on an as-needed basis when the processing device 42 executes a program for controlling the operation of the image pickup device 20. The storage device 44 may include a Random Access Memory (RAM), a Read Only Memory (ROM), etc.

FIG. 2 illustrates an example of a functional configuration of the image pickup device 20 according to the first embodiment. As explained by referring to FIG. 1, the image pickup device 20 includes the optical unit 30 having the illumination unit 31 and the camera 35. As illustrated in FIG. 2, the image pickup device 20 may make the storage device 44 store a database 46 and image information 48. The database 46 is for example a registration template used for biometric authentication. An example of a registration template is a biometric feature extracted from a palm vein image in the case when authentication is conducted on the basis of palm vein. When a plurality of authentication process are conducted on an identical biological body, it is also possible to store for example the palm vein information and palm print information as a registration template. The image information 48 may be stored in a buffer temporarily for example.

In the image pickup device 20, the processing device 42 has the functions as a management unit 50, a feature extraction unit 57, a matching unit 59 and an image processing unit 52. These functions may be realized by reading and executing a control program for controlling the image pickup device 20 stored in the storage device 44 beforehand.

The management unit 50 manages the processes of the entirety of the image pickup device 20 including the processes of biometric authentication. The image processing unit 52 generates images having information in response to depths from the surface such as for example images with different pieces of depth information on the basis of images picked up by the camera 35. The image processing unit 52 includes an image management unit 54 and an image computation unit 55. The image management unit 54 of the image processing unit 52 manages the entire image generation process. The image computation unit 55 executes an image computation process, which will be described later. The process performed by the image processing unit 52 will be explained in detail.

The feature extraction unit 57 extracts, from an image that was picked up, a biometric feature used for authentication. The matching unit 59 performs a matching process. In other words, the matching unit 59 uses a feature data extracted by the feature extraction unit 57 and outputs a similarity level, which represents how much data such as a registration template registered in a database 46 and information obtained from the picked-up image are similar to each other.

Next, explanations will be given for an image picked up by the camera 35 according to the first embodiment. Hereinafter, it is assumed that the scattering body serving as a subject is a biological body. First, only diffused reflection is examined. Diffused reflection used herein is reflection in which the light having entered the biological body passes through the biological body while repeating the scattering and enters the camera 35. Besides diffused reflection, surface reflection, in which light reflects between the biological body and air, exits.

FIG. 3 illustrates an example of the polarization angle dependence of incident light of the luminance value of a subject. The example illustrated in FIG. 3 is an example of a measurement result and is a result of measurement that used evaluation device for multi polarization having a configuration similar to that of the image pickup device 20. Note that filters of polarization angles θ=0°, 45°, 90° and 135° are used in the first embodiment, while measurements in units of 15° were conducted in FIG. 3.

As illustrated in FIG. 3, in polarization angle dependency 70 of luminance ratio, the horizontal axis corresponds to polarization angle θ, which represents the angle difference in the polarization direction of the multi-polarization filter 37 of the camera 35 with respect to the polarization direction of the polarization filter 33 of the illumination unit 31. In the present embodiment, the direction of the light cast on the scattering body is assumed to be polarization angle θ=0°. Accordingly, polarization angle θ, which represents the polarization direction of the light detected by the camera 35 for picking up an image of reflected light is the angle difference from the polarization direction of the light that is cast. The vertical axis represents the luminance ratio obtained by normalizing the luminance value at polarization angle θ by using the luminance value at polarization angle θ=90° as a reference.

The polarization angle dependency 70 of luminance ratio represents changes in luminance values (result of experiment) in a case when prescribed polarized light is cast on a scattering body such as a palm and images were picked up in different polarization directions on the camera side. A luminance ratio 72 and a luminance ratio 74 are results related to different subject persons. As described above, when the polarization direction of the light from the illumination and the polarization direction of the light picked up by the camera are the same, i.e., when the polarization angle θ=0 (polarization direction of incident light), the luminance value tends to be higher than that for the polarization angle θ=90°. Also, the luminance value changes continuously in the range of 0°≤θ≤90°, where θ represents the polarization angle.

Figure 4:
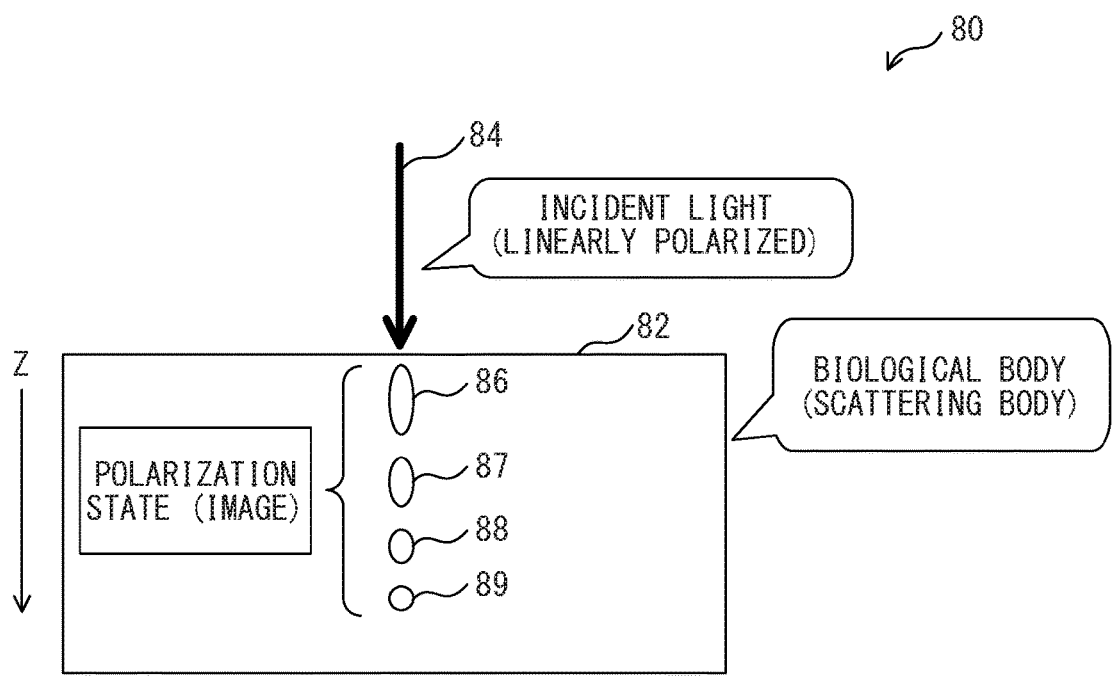
FIG. 4 illustrates changes of the polarization state in a biological body.

FIG. 4 illustrates changes of the polarization state in the biological body. As illustrated in FIG. 4, a scattering model 80 displays the image of the polarization state in a case when prescribed polarized light is incident in direction Z as depicted by light 84 incident on a scattering body 82 (biological body). It is illustrated that the closer to a circle each of polarization variation states 86 through 89 is, the greater the variation of polarization is. The scattering model 80 in the scattering body 82 is below. Specifically, it is a model in which light that was close to linearly polarized light when it was incident starts to gradually contain various polarization directions as depicted by the polarization variation states 86 through 89 as the light travels in direction Z (depth direction) and the variation of the polarization states becomes greater.

Luminance value I(θ) at polarization angle θ is expressed by expression 1 below and the derivation will be explained later in detail. Note that luminance value I(0°) and luminance value I(90°) of the light are luminance values at polarization angle θ=0° and polarization angle θ=90°, respectively.

$$I(\theta)=I(0°)\cos^2\theta+I(90°)\sin^2\theta \quad \text{(expression 1)}$$

In other words, the scattering light at arbitrary polarization angle θ is obtained by the linear combination between luminance value I(0°) and luminance value I(90°), and the coefficients thereof are $\cos^2\theta$ and $\sin^2\theta$. An image picked up at polarization angle θ=0° is an image picked up by a camera in the polarization direction that is the same as the polarization direction of the illumination light. In other words, it is an image picked up with light in which the polarization direction set under the illumination remains. Accordingly, it contains much information of a shallow position of the subject. An image picked up at polarization angle θ=90° is an image picked up with light whose polarization state of the illumination has been lost completely and contains much information of a deeper position of the subject.

<Scattering Body Model>

Hereinafter, explanations will be given for a derivation method of expression 1. In the present embodiment, the following physical model is assumed in order to explain changes of the luminance value at polarization angles θ. In other words, a case in which the illumination light that received linear polarization is incident on a biological body (scattering body) is described. The light having entered the biological body travels in the biological body while receiving scattering. It is believed that the polarization state gradually becomes random at higher rate from the linear polarization in response to the depth. Specifically, it is believed that light returning from a portion very shallow from the surface maintains the polarization state mostly. And, it is expected that light returning from a portion deep in a biological body has the polarization state broken mostly and the polarization direction has become random. Accordingly, it is believed that an image picked up by a polarization camera such as the camera 35 is picked up in a situation where the above types of light are mixed.

<Discussion of Polarization Angle Dependency of Luminance Value>

As described in FIG. 3, when images are picked up while changing polarization angle θ of received light with polarization illumination light cast on a biological body such as a palm, the illumination light having been polarized in a prescribed direction, the average luminance value changes smoothly. When polarization angle θ=0°, which is the same as that of the incident light, the luminance value is the highest, and when polarization angle θ=90°, which is orthogonal to the incident angle, the luminance value is the lowest. This polarization angle θ dependency of luminance value will be discussed with references to the above physical model.

First, probability density function f(z) that represents the depth in the biological body from which light returns is defined. This is a function that results in f(z)dz as the probability that the light cast on a biological body returns from a portion with the depth between z through (z+dz). Note that a specific form of probability density function f(z) is unknown, however, an example of calculation of a related probability density function by diffusion approximation is described in for example non Patent Document 2.

According to the above assumed physical model, the polarization state of the light having entered the biological body has a rate of the state that has deteriorated more from the linear polarization with an increasing depth. As a shape representing this variation of the polarization state, an ellipse is assumed.

Figure 5:
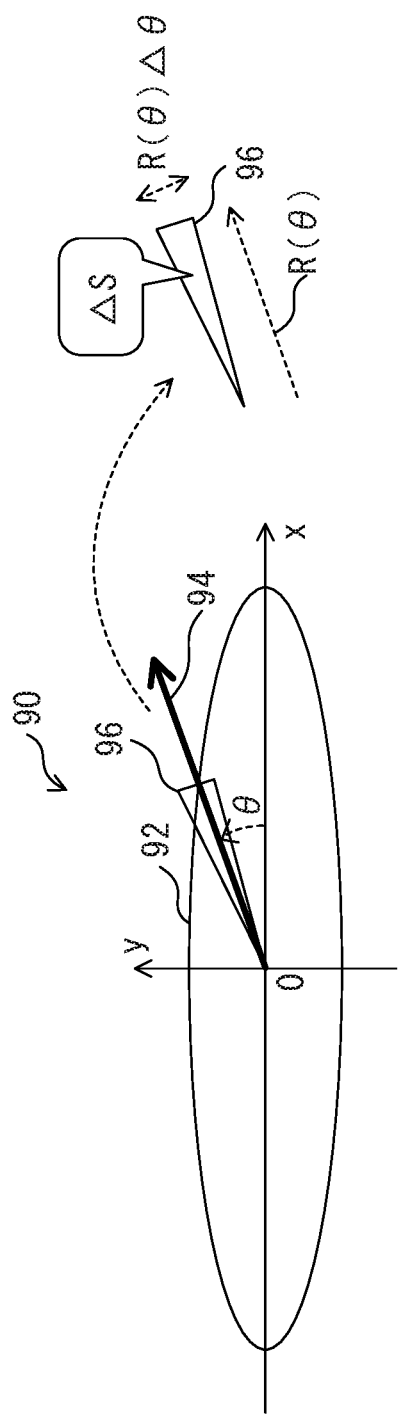
FIG. 5 illustrates an example of a rate occupied by polarization angle θ.

FIG. 5 illustrates an example of a rate occupied by polarization angle θ. In for example plane xy that is orthogonal to the traveling direction of the light having been incident on the biological body, a polarization variation image 92 is assumed as an ellipse that is a shape representing the polarization variation as illustrated in FIG. 5. The ellipse of the polarization variation image 92 is expressed by two parameters, i.e., major axis a and minor axis b. In this situation, it is possible to assume that major axis a represents the light in polarization direction θ=0° while minor axis b represents polarized light in polarization direction θ=90°. It is thought that the polarization state has been lost completely and the ellipse has changed into a circle at a portion with sufficient depth. Therefore, it is possible to express major axis a and minor axis b by expressions (2) below, which are functions of depth z.

$$a=a(z), \ b=b(z) \quad \text{(expression 2)}$$

It is now discussed how luminance value I(θ) at arbitrary polarization angle θ is expressed. It is assumed that the variation state of the polarization direction is an ellipse in a case when the polarization state of the light having received linear polarization has deteriorated. For example, it is possible to assume that this ellipse represents the distribution of the amounts of light at polarization angles θ. In this situation, it is possible to assume that S=πab is satisfied, where S represents the area of the ellipse. It is also possible to assume that the amount of light at arbitrary polarization angle θ is the area of a minute sector that is extracted in accordance with a polarization direction 94, such as for example a minute area 96.

The minute area 96 partitioned by minute angle Δθ in the direction of polarization angle θ of the polarization direction 94 can be obtained as blow. First, R(θ) can be expressed by expression 3 below, where the diameter of the ellipse at polarization angle θ is represented by R(θ).

$$R(\theta) = \sqrt{a(z)^2 \cos^2(\theta) + b(z)^2 \sin^2(\theta)} \quad \text{(expression 3)}$$

Also, when the minute area 96 of the sector extracted at minute angle Δθ is area θS, area ΔS can be obtained by approximating the ellipse by a circle as in expression 4 below, where minute angle Δθ is a constant representing the bandwidth of the polarization filter. In other words, the bandwidth used for making the polarized light at θ±(½)Δθ transmitted as the polarization filter is Δθ.

$$\Delta S = (\tfrac{1}{2}) R(\theta)^2 \Delta\theta \quad \text{(expression 4)}$$

From the above discussion, ratio (θ) of the light amount occupied by the polarized light in the polarized angle θ direction can be obtained by expression 5 below, where ratio (θ) is a ratio occupied by the amount of the light in the polarization angle θ direction when the entire light amount is the light amount that corresponds to luminance value $I_0$.

$$\begin{aligned}
\text{ratio}(\theta) &= \frac{\Delta S}{S} \quad \text{expression (5)}\\
&= \frac{1}{2} \frac{R(\theta)^2}{\pi a(z) b(z)} \Delta\theta\\
&= \frac{1}{2} \frac{a(z)^2 \cos^2\theta + b(z)^2 \sin^2\theta}{\pi a(z) b(z)} \Delta\theta\\
&= \frac{\Delta\theta}{2\pi} \left( \frac{a(z)}{b(z)} \cos^2\theta + \frac{b(z)}{a(z)} \sin^2\theta \right)
\end{aligned}$$

In order to simplify the expression, function s(z), which represents the ratio between major axis a(z) and minor axis b(z), is defined as expression 6. Note that function ε(z) satisfies the relationship of expression 7 below.

[Numerical expression 3]

$$\varepsilon(z) = \frac{a(z)}{b(z)} \quad \text{(expression 6)}$$

$$\varepsilon(z) \geq 1.0 \quad \text{(expression 7)}$$

Ratio (θ) is defined as in expression 8 below by using function ε(z).

$$\text{ratio}(\theta) = \frac{\Delta\theta}{2\pi} \left( \varepsilon(z) \cos^2\theta + \frac{1}{\varepsilon(z)} \sin^2\theta \right) \quad \text{(expression 8)}$$

The ratio occupied by the amount of light in the polarization direction θ in the entire light is obtained as above.

Here, luminance value I(θ) of the reflection light picked up as the total of the reflected light from various depths z is obtained. Luminance value I(θ) of the reflection light can be expressed as integral as in expression 9 below by using above probability density function f(z), ratio (θ) and constant $I_0$ that expresses the entire light amount.

$$\begin{aligned}
I(\theta) &= I_0 \int_0^\infty f(z) \times \text{ratio}(\theta) \, dz \quad \text{(expression 9)}\\
&= \frac{\Delta\theta I_0}{2\pi} \int_0^\infty f(z) \left( \varepsilon(z) \cos^2\theta + \frac{1}{\varepsilon(z)} \sin^2\theta \right) dz\\
&= \cos^2\theta \frac{\Delta\theta I}{2\pi} \int_0^\infty f(z) \varepsilon(z) \, dz + \sin^2\theta \frac{\Delta\theta I_0}{2\pi} \int_0^\infty f(z) \frac{1}{\varepsilon(z)} \, dz
\end{aligned}$$

Luminance values at θ=0° and θ=90° are obtained by expression 10 below. They are luminance values in cases when the polarization direction is parallel and orthogonal to the illumination light.

$$\begin{aligned}
I(0°) &= \frac{\Delta\theta I_0}{2\pi} \int_0^\infty f(z) \varepsilon(z) \, dz \quad \text{(expression 10)}\\
I(90°) &= \frac{\Delta\theta I_0}{2\pi} \int_0^\infty f(z) \frac{1}{\varepsilon(z)} \, dz
\end{aligned}$$

Substituting the values in expression 10 into expression 9 results in the relationship as expressed by expression 11 below that includes expression 1 above.

$$\begin{aligned}
I(\theta) &= I(0°) \cos^2\theta + I(90°) \sin^2\theta \quad \text{(expression 11)}\\
&= (I(0°) - I(90°)) \cos^2\theta + I(90°)
\end{aligned}$$

Specifically, it is understood that the luminance value at polarization angle θ is proportional to $\cos^2\theta$. Also, the image at arbitrary polarization angle θ is synthesized from two images at θ=0° and θ=90°. It is believed that this characteristic is derived from the additivity of light. Specifically, in expression 9 that obtains the luminance value in the polarization angle θ direction, luminance value I(θ) is obtained by integrating a minute area in the polarization angle θ direction that is the calculation target. Because polarization angle θ and depth z are independent variables, the process of obtaining the ratio in the polarization angle θ direction to integrate it in the z direction and the process of conducting the integration in the z direction and thereafter obtaining the ratio in the polarization angle θ direction are identical. The result of conducting the integration in the z direction first is defined as luminance values I(0°) and I(90°), and the luminance value at polarization angle θ is defined as expression 11 (or expression 1) that has a form of linearly combining both of them.

Figure 6:
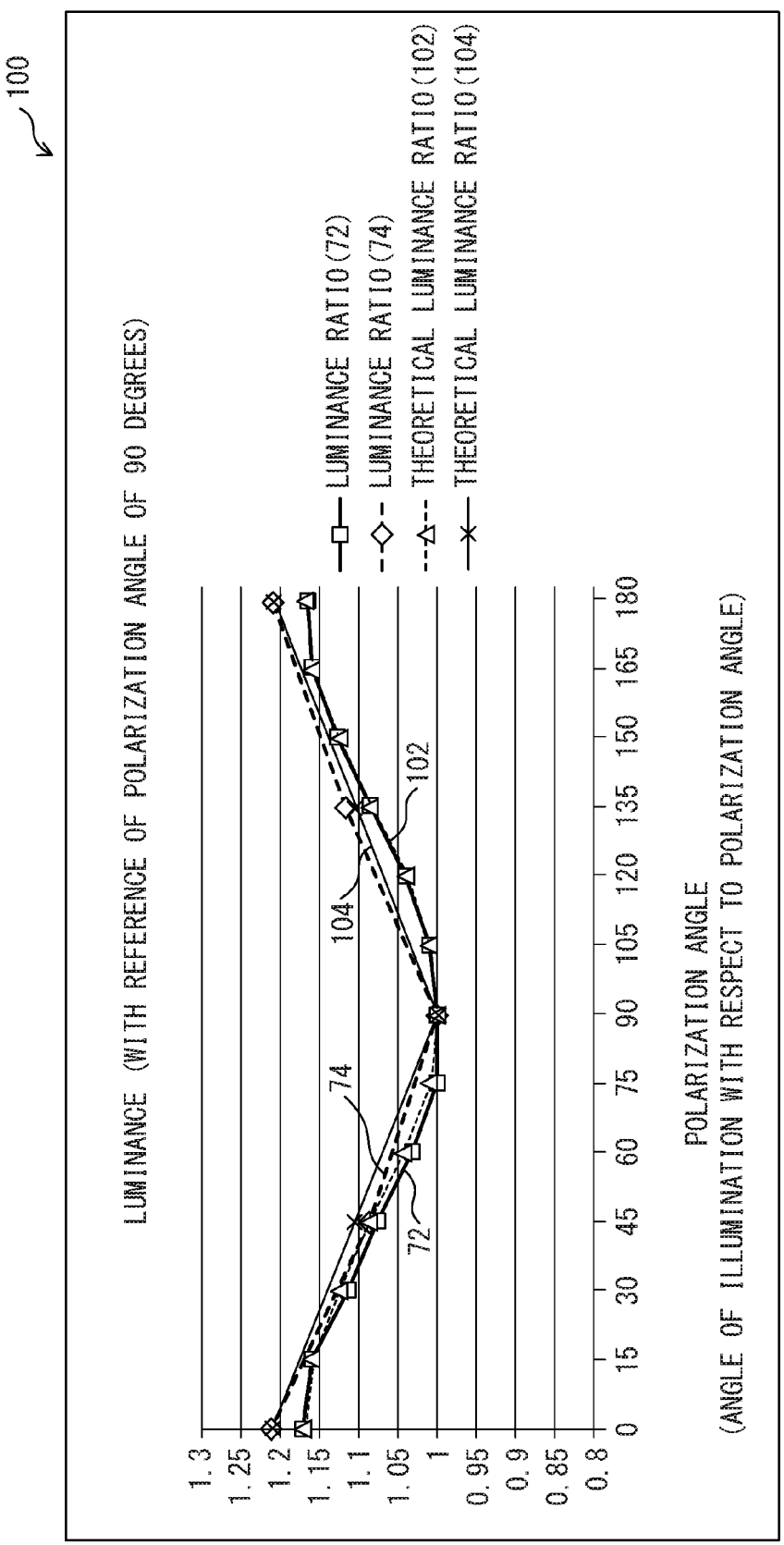
FIG. 6 illustrates a comparison example of measured values and theoretical values of the polarization angle θ dependence of the luminance ratio.

FIG. 6 illustrates a comparison example of measured values and theoretical values of the polarization angle θ dependence of the luminance ratio. In FIG. 6, the horizontal axis represents polarization angle θ, which represents the angle difference in the polarization direction of the multi-polarization filter 37 of the camera 35 with respect to the polarization direction of the polarization filter 33 of the illumination unit 31. The vertical axis represents the luminance ratio at polarization angle θ normalized by using the luminance value at polarization angle θ=90° as a reference. In FIG. 6, theoretical luminance ratios 102 are theoretical values obtained from the measured values at 0° and 90° at the luminance ratio 72, and theoretical luminance ratios 104 are theoretical values obtained from the measured values at 0° and 90° at the luminance ratio 74. As illustrated in FIG. 6, the luminance ratio 72 and the luminance ratio 74, which are measured values, display generally good correspondence to the theoretical luminance ratio 102 and the theoretical luminance ratio 104, which are theoretical values.

As described above, it is desirable to use the above physical model as a model representing luminance values in a case when linearly polarized light is cast on a scattering body such as a biological body and the reflection light is picked up at a plurality of polarization angles θ. In other words, by expressing as an ellipse the process in which the degree of polarization is reduced with an increasing depth on an assumption that the biological body is a scattering reflective object, results displaying good correspondence to the experiments can be obtained. Expression 1 is described again below for the convenience of explanation.

$$I(\theta) = I(0°)\cos^2 \theta + I(90°)\sin^2 \theta \quad \text{(expression 1)}$$

Expression 1 indicates that the luminance value at arbitrary polarization angle θ is obtained from two luminance values, i.e., I(0°) and I(90°). Hereinafter, a method of picking up an image that brings more information is discussed by using the relational expression expressed by expression 1. In the discussion, for example a multi-polarization camera manufactured by Photonic Lattice, Inc. as described in non Patent Document may be used as the camera 35. According to a multi-polarization camera manufactured by Photonic Lattice, Inc., polarization images in four directions at polarization angles θ of 0°, 45°, 90° and 135° are obtained simultaneously. This multi-polarization camera is provided with a polarization filter for each pixel of an image pickup element instead of a Bayer filter for a color camera. Specifically, a set of four filters at polarization angles θ=0°, 45°, 90° and 135° is provided.

In the present embodiment, for example a method of obtaining more effective information including the images at polarization angles of 45° and 135°, which has not been used so much, is discussed. As a specific proposal of a method of picking up an image, the following method may be possible.

The discussion above has treated only the diffused reflection from a biological body. However, surface reflection actually exits in addition to diffused reflection. Surface reflection is caused by a difference in the refraction index between the air and a subject. Surface reflection has a characteristic of maintaining a polarization state, and accordingly surface reflection is used only for picking up images at polarization angle θ=0°. Accordingly, images picked up by a multi-polarization camera such as the camera 35 (θ=0°, 45°, 90° and 135°) are as below. Note that subscript "C" represents an image picked up by a camera and subscript "SP" represents surface reflection. Symbols without subscripts represent diffused reflection components.

$$I_C(0°) = I(0°) + I_{SP}$$

$$I_C(45°) = I(45°)$$

$$I_C(90°) = I(90°)$$

$$I_C(135°) = I(135°) \quad \text{(expression 12)}$$

Now, θ=45° and 135° is input to expression 1.

$$I(45°) = \frac{1}{2}I(0°) + \frac{1}{2}I(90°)$$

$$I(135°) = \frac{1}{2}I(0°) + \frac{1}{2}I(90°) \quad \text{(expression 13)}$$

When the right-hand member and the left-hand member of expression 13 are added, diffused reflection components alone are obtained at θ=0° as below.

$$I(0°) = I(45°) + I(135°) - I(90°) \quad \text{(expression 14)}$$

In other words, the diffused reflection components at θ=0° is calculated from the images at θ=45°, 90° and 135°. Further, the surface reflection component can be obtained from this expression as below.

$$I_{SP} = I_C(0°) - I(0°) \quad \text{(expression 15)}$$
$$= I_C(0°) - (I_C(45°) + I_C(135°) - I_C(90°))$$

As described above, luminance value $I_{SP}$ based on the surface reflection, luminance value I(0°) corresponding to information of a shallow position and luminance value I(90°) corresponding to information of a deep position are obtained. As described above, there is a possibility that more authentication features are obtained from three images respectively corresponding to different depths.

FIG. 7 illustrates an example of a type of an image obtained by the image pickup method according to the first embodiment. As illustrated in FIG. 7, in an image type 110, it is illustrated that surface information, shallow information and deep information are obtained by the image pickup device 20 according to the present embodiment. An example of surface information may be palm print information. An example of deep information may be vein information etc. It is possible to conceive that shallow information is used for detecting identity thefts in a case when a print piece etc. of a palm print is used instead of the real hand or in a case when shallow information is not obtained for authentication that uses palm print information is used.

Specifically, surface reflection is obtained by expression 15, and is used as for example palm print information etc. as the surface information corresponding to an image of the scattering body. Information of a shallow position is obtained by for example expression 14, and is used as shallow information corresponding to a first inner layer image of a relatively shallow position in inner layer information of the scattering body. Information of a deep position is obtained by expression 12, corresponds to a second inner layer image of a deep position, which is more distant from the surface than is the above shallow position, in inner layer information of the scattering body and is used as for example vein information etc.

Note that obtaining only the diffused reflection light as luminance value I(0°) when polarization angle=0° is a feature of the image pickup device 20 according to the present embodiment. When an image is picked up simply by setting polarization angle θ to zero degree, an image in which the diffused reflection and the surface reflection are mixed is obtained. Surface reflection brings about the advantage that information related to the subject surface can be obtained, but has a characteristic that the strength sharply changes depending upon the positional relationship between the subject, the illumination and the camera. This may lead to a disadvantage that image information obtained by using surface reflection is not suitable for authentication processes depending upon the setting conditions of devices. By contrast, according to the present embodiment, it is possible to obtain luminance value I(0°) that does not contain surface reflection.

Note that in the above explanations, methods using the four directions (0°, 45°, 90° and 135°) as the input to the camera 35 was used. This is based on a specification of a commercially available multi-polarization camera such as the camera described in non Patent Document 1. However, images in three directions can implement the calculation of the above three types of images. The three directions of for example 0°, 45° and 90° are enough. Specifically, it is sufficient to substitute 45° into expression 1. Specifically, it is expressed by expressions 16 below.

$$I(45°)=½×I(0°)+½×I(90°)$$

$$I(0°)=2×I(45°)-I(90°) \quad \text{(expression 16)}$$

Expression 16 corresponds to a case when I(135°)=I(45°) is satisfied in expression 14. As a general rule, using two images of 45° and 135° as represented by expression 15 results in better image quality. This is because images always include noise and using a plurality of images (45° and 135°) can reduce influence of noise.

<Variation of Image Calculation>

The above explanation uses a case when the difference of the angle between the filters in the camera 35 is 45°. When there is the difference of 45°, both $\cos\theta$ and $\sin\theta$, which are coefficients of expression 1, are $1/\sqrt{2}$. Therefore, both coefficients become (½) when they are squared, making the calculation easier. However, the image pickup method of the present embodiment is not limited to the case with 45° as the angle difference between filters and combinations between other angles may be used.

Hereinafter, a case of a combination between θ=0°, 30° and 60° will be discussed as an example of a combination between other angles. The luminance values representing images picked up by the camera are as below.

$$I_C(0°)=I(0°)+I_{SP}$$

$$I_C(30°)=I(30°)$$

$$I_C(60°)=I(60°) \quad \text{(expression 17)}$$

Here, θ=30° and 60° are input to expression 1 that is satisfied for diffused reflection components.

$$I(30°) = \frac{3}{4}I(0°) + \frac{1}{4}I(90°) \quad \text{(expression 18)}$$

$$I(60°) = \frac{1}{4}I(0°) + \frac{3}{4}I(90°)$$

I(0°) and I(90°) are obtained from expression 18.

$$I(0°) = \frac{3}{2}I(30°) - \frac{1}{2}I(60°) \quad \text{(expression 19)}$$

$$I(90°) = -\frac{1}{2}I(30°) + \frac{3}{2}I(60°) \quad \text{(expression 20)}$$

As described above, luminance value I(0°) corresponding to an image of information of a shallow position without surface reflection can be calculated from luminance values (I(30°), I(60°)) corresponding to images to be picked up. Thereby, luminance value $I_{SP}$ of surface reflection components are obtained by calculation similar to the method illustrated for the image type 110.

From the above, it is understood that polarization angle θ of images to be picked up can be set to various directions. Note that in order to obtain surface information, image of θ=0° is to be included. This is because surface reflection components are believed to be included only in θ=0°. It is also possible to set two polarization angles $\theta_1$ and $\theta_2$ other than θ=0° ($\theta_1$ and $\theta_2$ are 30° and 60°, respectively in the above example) in such a manner that $\theta_1±\theta_2=90°$ is satisfied. Using polarization angles $\theta_1$ and $\theta_2$ in such a relationship brings about an advantage of being able to simplify coefficients of the calculation.

Further, because luminance values I(0°) and I(90°) are obtained from expressions 19 and 20, an image corresponding to arbitrary polarization angle θ can be obtained by applying expression 1. The obtained image corresponding to polarization angle θ includes information of an intermediate depth of the images respectively corresponding to luminance values I(0°) and I(90°).

Figure 8:
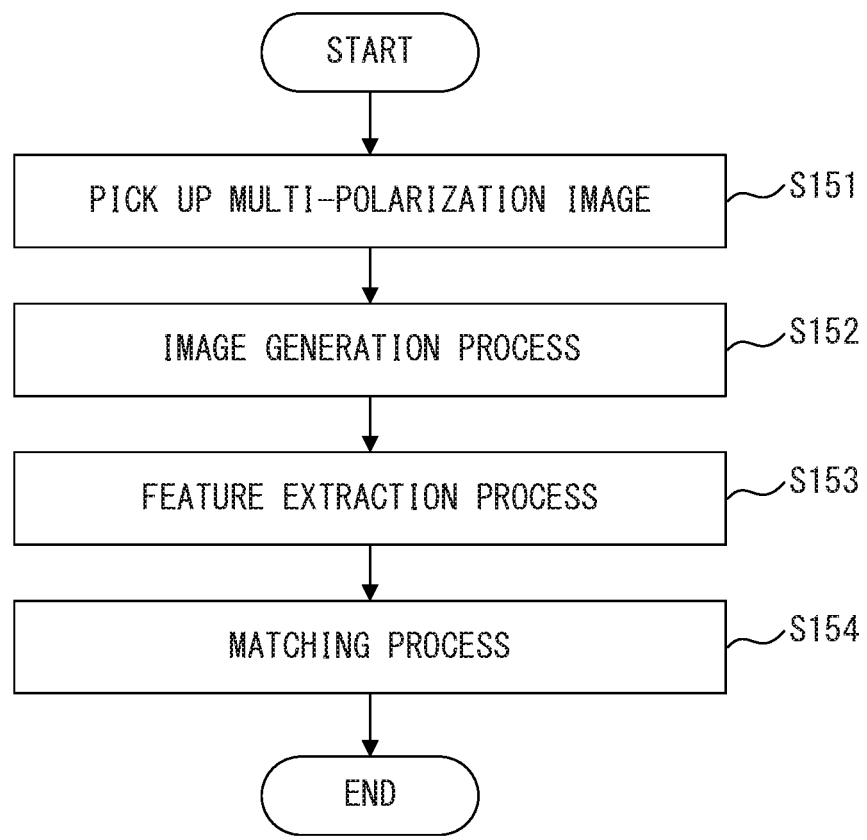
FIG. 8 is a flowchart illustrating an example of a biometric authentication process according to the first embodiment.

Next, by referring to a flowchart, a biometric authentication method that uses the image pickup device 20 according to the present embodiment will be explained. FIG. 8 is a flowchart showing an example of a biometric authentication process according to the first embodiment. In the biometric authentication process, the control unit 40 picks up multi-polarization images at appropriate positions. Specifically, the camera 35 such as for example a multi-polarization camera etc. is used so as to pick up polarization images in a plurality of polarization directions. In other words, the camera 35 picks up images based on polarization in a plurality of directions including at least three directions including the polarization angle that is the same as that of the illumination light cast on the subject (S151).

The image processing unit 52 conducts an image generation process (S152). The image generation process is a process that generates an image at arbitrary polarization angle θ based on images picked up in for example the three polarization directions as described above. For example, the image computation unit 55 of the image processing unit 52 generates surface information, information of a shallow position, information of a deep position, etc. by using the computation method illustrated for the image type 110.

Specifically, each image is calculated as below.

i) Surface Image $$I_{SP}=I_C(0°)-(I_C(45°)+I_C(135°)-I_C(90°)) \quad \text{(expression 15)}$$

ii) Information of Shallow Position $$I(0°)-(I_C(45°)+I_C(135°)-I_C(90°)) \quad \text{(expression 15)}$$

iii) Information of Deep Position $$I(90°)=I_C(90°) \quad \text{(expression 21)}$$

As described above, only addition and subtraction of simple images are conducted and coefficients are not used.

The feature extraction unit 57 performs an extraction process of biometric authentication feature in a generated image (s153). It is desirable that various methods such as edge extraction, Matched Filter, a method using local feature amount, etc. be used as the feature extraction process.

The matching unit 59 calculates the similarity level by comparing the biometric feature extracted by the feature extraction unit 57 and a template registered in the database. As a method of calculating a similarity level, any of various calculation methods such as function coefficient, cross-correlation function, distance between images, etc. can be used (S154). For this, the matching unit 59 may conduct authorization by determining the type of a registered template on the basis of which image is used among i) through iii) above.

As described above, the image pickup device 20 according to the first embodiment includes the illumination unit 31 configured to cast prescribed polarized light on a scattering body, the camera 35 configured to pick up images of the scattering body at a plurality of different polarization angles, and the processing device 42. The processing device 42 generates and outputs an inner layer image in response to the depth from the surface of the scattering body of an inner layer of the inside of the scattering body on the basis of the images of the scattering body picked up at a plurality of polarization angles. Also, the processing device 42 may perform biometric authentication on the basis of images obtained by picking up an image of a biological body. An image for performing biometric authentication may be one of surface information, information of a shallow position and information of a deep position. Also, the storage device 44 may store a program for controlling the operation of the image pickup device 20, a registration template for biometric authentication, etc.

As described above, according to the image pickup device 20, three types of images with different depths of a scattering body such as a biological body can be obtained. For this, the image pickup device 20 for example picks up three images at different polarization angles. The image pickup device 20 can obtain an image at arbitrary polarization angle θ from picked up images. Obtaining an image at arbitrary polarization angle θ means that images of the surface of the scattering body and images with different depths in the scattering body can be obtained simultaneously. Accordingly, performing biometric authentication by using the image pickup device 20 brings about an advantage that an image appropriate for biometric authentication can be generated and authentication accuracy increases.

Biometric authentication utilizes the fact that a biological body does not include so much material that absorbs light in a wavelength band of near infrared rays and allows light to enter to a deep portion. Biological bodies have characteristics that cause a high level of scattering with respect to near infrared rays, sometimes resulting in a case when highly accurate information is not obtained due to the scattering. However, in the above computation, it is possible to obtain an image in a desired polarization direction that is calculated on the basis of images picked up in a plurality of polarization directions. Also, by using a physical model in which the greater the depth of the scattering light in the biological body is, the greater the variation in the polarization state due to the scattering in a biological body is, it is possible to assume a polarization state that includes more information of a desired depth. Accordingly, it is possible to obtain an image in response to the depth in the biological body more accurately. This makes it possible to obtain vein information of an inner layer of the biological body, palm print information of the surface of the biological body, etc. accurately, increasing the accuracy of biometric authentication.

As described above, "multi polarization technique" utilizing polarized light in a plurality of directions makes it possible to obtain more pieces of feature data. Specifically, by calculating and obtaining a plurality of images from one subject (such as a palm), it is possible to obtain more feature information from one subject. In particular because surface information, information of a shallow position and information of a deep position of a subject can be obtained individually, it is possible to further increase the authentication accuracy.

Also, obtaining images of different depths simultaneously brings about an advantage that when attention is paid to a point in an image, various pieces of depth information regarding the corresponding point can be obtained. Even when information of different depths are obtained time divisionally by using a method in which a plurality of illumination devices in different polarization directions are prepared and images are picked up by sequentially turning on such illumination devices or other methods, time differences exist between the obtained images. Accordingly, it is difficult to obtain correspondence information between the features at the identical points. However, according to the image pickup device 20, it is possible to obtain images of different depths at the same time and at the same point and to obtain correspondence information between the features at the same point.

When it is intended to pick up only an image at an arbitrary polarization angle θ, a method may be possible in which a polarization filter in the corresponding direction is set mechanically, however, a mechanism is to be used for setting a polarization filter to arbitrary polarization angle θ. By contrast, according to the image pickup device 20 of the present embodiment has an advantage that an image related to an arbitrary polarization angle can be obtained through computation alone. This eliminates the necessity of a mechanism. Also, as a general rule, it takes time to switch optical filters or illumination devices, while the image pickup device 20 does not use such time. As described above, the image pickup device 20 is an image pickup device that is advantageous in cost and maintenance.

Second Embodiment

Hereinafter, an image pickup device according to a second embodiment will be explained. In the second embodiment, the same configurations and operations as those in the first embodiment will be denoted by the same symbols, and overlapping explanations will be omitted. An example of a hardware configuration of an image pickup device 200 of the second embodiment is a configuration resulting from adding a display unit 270 to the same configuration as that of the image pickup device 20 according to the first embodiment.

Figure 9:
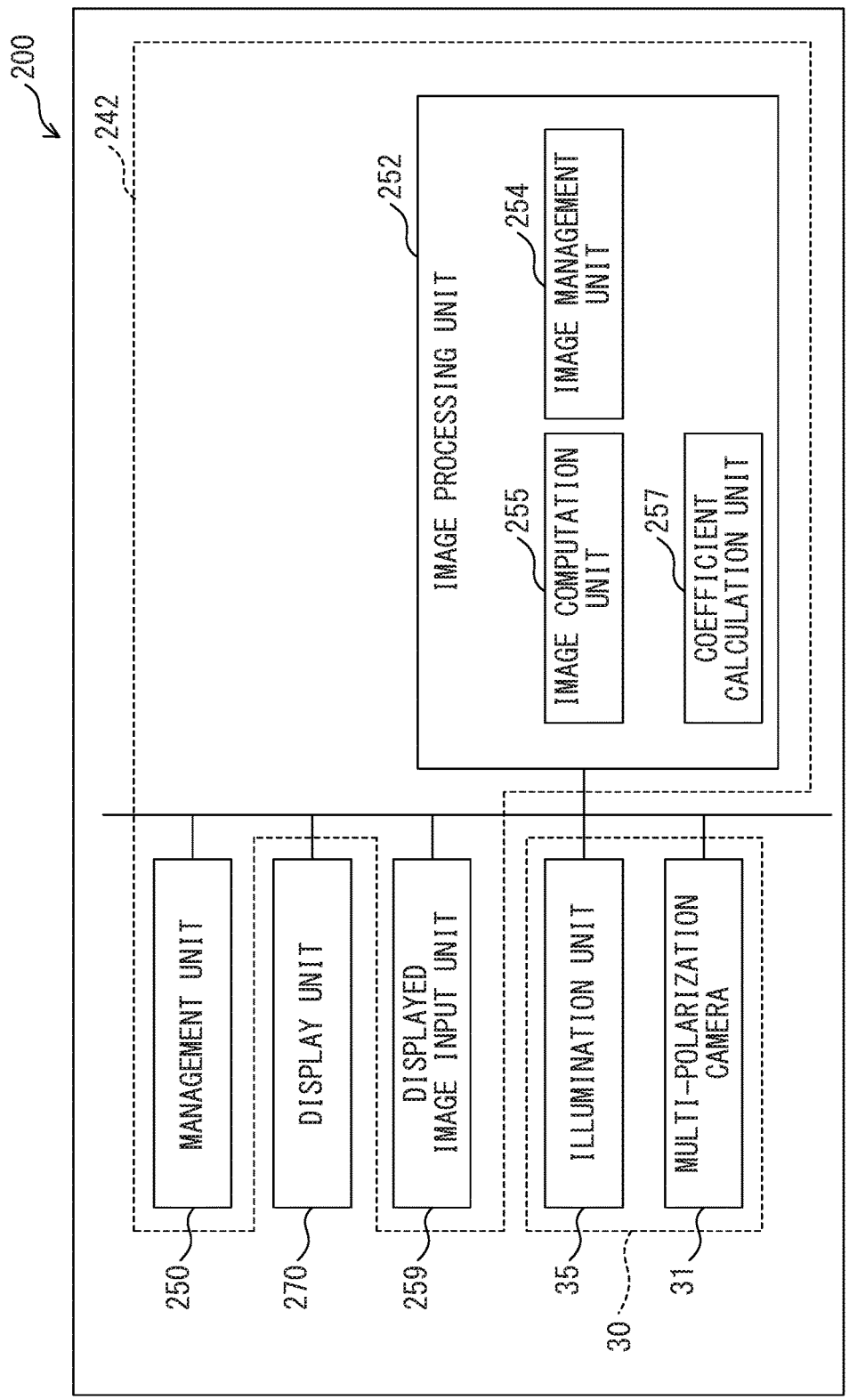
FIG. 9 illustrates an example of a functional configuration of an image pickup device of the second embodiment.

FIG. 9 illustrates an example of a functional configuration of the image pickup device 200 of the second embodiment. As illustrated in FIG. 9, the image pickup device 200 includes the optical unit 30, a processing device 242 and the display unit 270.

The processing device 242 may read and execute a control program stored in for example a storage device (not illustrated) so as to implement the respective functions illustrated in FIG. 9. The processing device 242 has the functions as a management unit 250, an image processing unit 252 and a display image input unit 259.

The display image input unit 259 inputs image information that the user desires to use. Specifically, a surface image or a diffusion image in desired polarization angle θ direction is selected so as to output it to the display unit 270. The display unit 270 may be for example a liquid crystal display device. The display unit 270 displays an image at arbitrary polarization angle θ.

The management unit 250 manages the entire process of the image pickup device 200. On the basis of images picked up by the camera 35, the image processing unit 252 generates images having different pieces of depth information.

The image processing unit 252 includes an image management unit 254, an image computation unit 255 and a coefficient calculation unit 257. The image management unit 254 of the image processing unit 252 manages the entire image generation process. The image computation unit 255 executes an image computation process similar to that executed by the image computation unit 55 according to the first embodiment. The coefficient calculation unit 257 calculates a calculation coefficient that corresponds to desired polarization angle θ input by the user of the image pickup device 200. This will be described later in detail.

In the present embodiment, the camera 35 picks up images in the three polarization directions at polarization angles θ=0°, 30° and 60°. The image computation unit 255 executes a process of generating images at arbitrary polarization angle θ on the basis of images in two polarization directions that were picked up. In other words, the image computation unit 255 conducts computation for generating the following images on the basis of the picked up images in a plurality of polarization directions. The computation expressions are as below.

α) surface image ($I_{SP}=I_C(0°)$, $I(0°)$ is based on expression 19)
β) diffused reflection image at polarization angle θ=0° (based on expression 19)
γ) diffused reflection image at polarization angle θ=90° (based on expression 20)
δ) image at polarization angle θ (θ≠0°, θ≠90°) (based on expression 1)

When expression 1 is used, it is desirable that the image pickup device 200 perform the calculation on an as-needed basis by using for example the coefficient calculation unit 257 by storing a table of cosine functions and sine functions in a storage device.

It is desirable that when the user has selected one of α) through δ) above, the image processing unit 252 generate the selected image through computation and make the display unit 270 display it via the display image input unit 259.

As described above in detail, the image pickup device 200 according to the second embodiment can make the display unit 270 display a desired image selected by the user. For this, similarly to the image pickup device 20 according to the first embodiment, the image pickup device 200 does not need mechanical components such as a mechanism for turning the polarization filter for changing the polarization direction while images are picked up. Therefore, the image pickup device 200 is advantageous in cost, maintenance, etc. in comparison with a device that uses a mechanism for turning the polarization filter.

Further, the image pickup device 200 calculates an image for arbitrary polarization angle θ in order to display it, and accordingly it is possible to obtain various pieces of information regarding the subject by changing the polarization angle θ or conducting computation based on images respectively corresponding to a plurality of polarization angles θ. For example, it is possible to obtain an image corresponding to information of an arbitrary depth of the subject. Further, it is also possible to use an obtained image for making a diagnosis in the medial field, testing the freshness of meat or fish, and for other purposes.

Variation Example

Hereinafter, a variation example will be explained. In the variation example, the same configurations and operations as those in the first or second embodiment will be denoted by the same symbols, and overlapping explanations will be omitted. The present variation example does not need to obtain a surface image. It is desirable that the hardware configuration of the image pickup device be similar to that of the image pickup device 20 or the image pickup device 200.

The first and second embodiments are both capable of obtaining a surface image. However, there is a case where a surface image is not used depending upon the purpose of picking up images. In such a case, a configuration that originally picks up images in polarization directions not including the surface reflection can be used. In such a case, only two polarization angles $\theta_1$ and $\theta_2$ are used as polarization directions for picking up images ($\theta_1$, $\theta_2 \neq 0°$).

Hereinafter, a specific computation method is described. First, polarization images picked up by the camera 35 are as expressed by expressions 22 below.

$I_C(\theta_1)=I(\theta_1)$ $I_C(\theta_2)=I(\theta_2)$ \hfill (expression 22)

Here, polarization angle $\theta=\theta_1$ and $\theta_2$ are substituted into expression 1 that is satisfied for diffused reflection components.

$I(\theta_1)=I(0°)\cos^2 \theta_1 + I(90°)\sin^2 \theta_1$ $I(\theta_2)=I(0°)\cos^2 \theta_2 + I(90°)\sin^2 \theta_2$ \hfill (expression 23)

Solving this expression for I(0°) and I(90°) results in expression 24 below.

$$I(0°) = \frac{\sin^2\theta_2 I(\theta_1) - \sin^2\theta_1 I(\theta_2)}{\cos^2\theta_1 \sin^2\theta_2 - \sin^2\theta_1 \cos^2\theta_2}$$ (expression 24)

$$I(90°) = \frac{-\cos^2\theta_2 I(\theta_1) + \cos^2\theta_1 I(\theta_2)}{\cos^2\theta_1 \sin^2\theta_2 - \sin^2\theta_1 \cos^2\theta_2}$$

As described above, the present variation example makes it possible to obtain an image in arbitrary polarization direction on the basis of images at polarization angles of two different directions. Thereby, it is possible to obtain an image of the inside of a scattering body more simply and to expand application scope including biometric authentication.

Note that the present invention is not limited to the above embodiments and can employ various configuration or embodiments without departing from the spirit of the present invention. For example, the orders of the processes explained above are not limited to the orders explained above. Also, the configurations of the devices can be modified when similar effects are achieved.

Also, in the explanations for the first and second embodiments and for the variation example, the illumination unit 31 casts illumination light at a polarization angle in a prescribed dereliction and images in different polarization directions are obtained by using a multi-polarization camera such as the camera 35 as an image pickup device. Images in different polarization directions used herein are images in polarization directions in which θ>0 is satisfied, with θ being 0° as the polarization direction of the illumination. However, it is possible to switch the functions of the illumination unit 31 and the camera 35 with each other. Specifically, the camera includes a polarization filter so as to pick up images only in a prescribed polarization direction. The illumination side includes a mechanism that casts illumination in different polarization directions. Specifically, illumination devices having filters for respective polarization directions are prepared independently so that light is cast while turning on the illumination devices at different timings.

In the above configuration, it takes time to turn on each illumination device in a different polarization direction, increasing time taken for picking up images. However, the image pickup device can be assembled inexpensively.

As described above, according to an embodiment, it is possible to obtain information of an inner layer in response to the depth from the surface of a scattering body.

All examples and conditional language provided herein are intended for the pedagogical purposes of aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although one or more embodiments of the present invention have been described in detail, it should be understood that the various changes, substitutions, and alterations could be made hereto without departing from the spirit and scope of the invention.

What is claimed is:

1. An image pickup device comprising:
   an illumination device that casts light of a prescribed polarization direction on a scattering body, the illumination device including a light source and a polarization filter;
   a camera that, while the illumination device is casting light of the prescribed polarization direction on the scattering body, picks up a plurality of images of the scattering body at a plurality of different polarization angles that allow light of a polarization direction that is different from the prescribed polarization direction to be transmitted; and
   a processor that, on the basis of the plurality of images, generates at least one inner layer image of an inner layer of an inside of the scattering body for a different polarization angle from the plurality of different polarization angles, and that outputs the at least one inner layer image.

2. The image pickup device according to claim 1, wherein
   the at least one inner layer image includes a first inner layer image of the scattering body that corresponds to a polarization angle of 0° and a second inner layer image of the scattering body that corresponds to a polarization angle of 90°, and
   the processor further generates, on the basis of the first inner layer image and the second inner layer image, a third inner layer image of the scattering body for an arbitrary polarization angle that is neither 0° nor 90°, and outputs the generated image.

3. The image pickup device according to claim 1, wherein
   the camera further picks up an image at an polarization angle that allows light of the prescribed polarization direction while the illumination device is casting light of the prescribed polarization direction on the scattering body;
   the processor further generates and outputs a surface image corresponding to the surface of the scattering body on the basis of the plurality of images of the scattering body picked up at the plurality of different polarization angles and the image picked up at the polarization angle.

4. The image pickup device according to claim 1, wherein
   the plurality of images include a first inner layer image corresponding to a first inner layer in the scattering body and a second inner layer image corresponding to a second inner layer that is more distant from the surface than is the first inner layer.

5. The image pickup device according to claim 1, the image pickup device further comprising:
   a memory that stores a surface reference image corresponding to the surface of the scattering body and an inner reference image corresponding to the inner layer of the scattering body, wherein
   the processor determines which of the surface reference image corresponding to the surface and the inner reference image corresponding to the inner layer is to receive evaluation of similarity to the plurality of images picked up at the plurality of polarization angles, and performs an authentication process by evaluating a level of similarity of reference images.

6. An image pickup method comprising:
   casting, by an illumination device, light of a prescribed polarization direction on a scattering body;
   picking up, by a camera, a plurality of images of the scattering body at a plurality of different polarization angles; and
   generating, by a processor and on the basis of the plurality of images, at least one inner layer of an inner layer of an inside of the scattering body for a different polarization angle from the plurality of different polarization angles, and that outputs the at least one inner layer image.

* * * * *